United States Patent
Fletcher

(10) Patent No.: US 11,447,432 B2
(45) Date of Patent: Sep. 20, 2022

(54) PROCESS TO PREPARE PROPYLENE

(71) Applicant: GASOLFIN B.V., Amersfoort (NL)

(72) Inventor: Raymond Paul Fletcher, Dusseldorf (DE)

(73) Assignee: GASOLFIN B.V., Amersfoort (NL)

( * ) Notice: Subject to any disclaimer, the term of this patent is extended or adjusted under 35 U.S.C. 154(b) by 392 days.

(21) Appl. No.: 16/470,321

(22) PCT Filed: Dec. 19, 2017

(86) PCT No.: PCT/NL2017/050845
§ 371 (c)(1),
(2) Date: Jun. 17, 2019

(87) PCT Pub. No.: WO2018/117820
PCT Pub. Date: Jun. 28, 2018

(65) Prior Publication Data
US 2020/0087228 A1 Mar. 19, 2020

Related U.S. Application Data

(60) Provisional application No. 62/437,242, filed on Dec. 21, 2016.

(30) Foreign Application Priority Data

Jan. 30, 2017 (NL) ..................................... 2018256

(51) Int. Cl.
| | |
|---|---|
| *C07C 4/06* | (2006.01) |
| *B01J 29/70* | (2006.01) |
| *B01J 29/76* | (2006.01) |
| *B01J 37/04* | (2006.01) |
| *B01J 37/08* | (2006.01) |
| *B01J 37/30* | (2006.01) |
| *C07C 5/27* | (2006.01) |

(52) U.S. Cl.
CPC .................. *C07C 4/06* (2013.01); *B01J 29/70* (2013.01); *B01J 29/76* (2013.01); *B01J 37/04* (2013.01); *B01J 37/08* (2013.01); *B01J 37/30* (2013.01); *C07C 5/2708* (2013.01); *B01J 2229/183* (2013.01); *C07C 2521/04* (2013.01); *C07C 2521/08* (2013.01); *C07C 2521/12* (2013.01); *C07C 2527/167* (2013.01); *C07C 2529/072* (2013.01); *C07C 2529/40* (2013.01)

(58) Field of Classification Search
CPC ..... C07C 4/06; C07C 5/2708; C07C 2521/04; C07C 2521/08; C07C 2521/12; C07C 2527/167; C07C 2529/072; C07C 2529/40; C07C 5/222; B01J 29/70; B01J 29/76; B01J 37/04; B01J 37/08; B01J 37/30; B01J 2229/183; B01J 29/405; B01J 2229/42; B01J 29/46; Y02P 20/52; C10G 45/64; C10G 69/04; C10G 55/06; C10G 2300/1081; C10G 2400/20; C10G 11/10; C10G 11/05

See application file for complete search history.

(56) References Cited

U.S. PATENT DOCUMENTS

| | | | | |
|---|---|---|---|---|
| 6,177,374 | B1 * | 1/2001 | Pradhan ................. | B01J 29/061 |
| | | | | 423/705 |
| 2008/0308455 | A1 * | 12/2008 | Long ...................... | C10G 11/05 |
| | | | | 208/120.35 |
| 2009/0099398 | A1 * | 4/2009 | Wegerer .................... | C07C 4/06 |
| | | | | 585/313 |
| 2012/0029251 | A1 * | 2/2012 | Hemighaus ............... | C10L 1/04 |
| | | | | 585/14 |
| 2014/0353216 | A1 * | 12/2014 | Scibola ..................... | C07C 7/08 |
| | | | | 208/354 |
| 2015/0174565 | A1 | 6/2015 | Hodoshima et al. | |
| 2017/0252731 | A1 * | 9/2017 | Hodoshima ............ | B01J 35/026 |

FOREIGN PATENT DOCUMENTS

WO 2016209074 A1 12/2016

OTHER PUBLICATIONS

Villegas et al. "Isomerisation of n-butane to isobutane over Pt-modified Beta and ZSM-5 zeolite catalysts: Catalyst deactivation and regeneration." Chemical Engineering Journal 120(1-2): 83-89 (2006).

* cited by examiner

*Primary Examiner* — Thuan D Dang
(74) *Attorney, Agent, or Firm* — Nixon Peabody LLP; Ronald I. Eisenstein; Nicole D. Kling

(57) ABSTRACT

The invention is directed to a process to prepare propylene from a hydrocarbon feed comprising pentane by contacting the hydrocarbon feed with a heterogeneous cracking catalyst as present in one or more fixed beds thereby obtaining a cracked effluent. The heterogeneous catalyst comprises a matrix component and a molecular sieve comprising framework alumina, framework silica and a framework metal selected from the group of Zn, Fe, Ce, La, Y, Ga and/or Zr. Propylene is isolated from the cracked effluent.

20 Claims, 1 Drawing Sheet

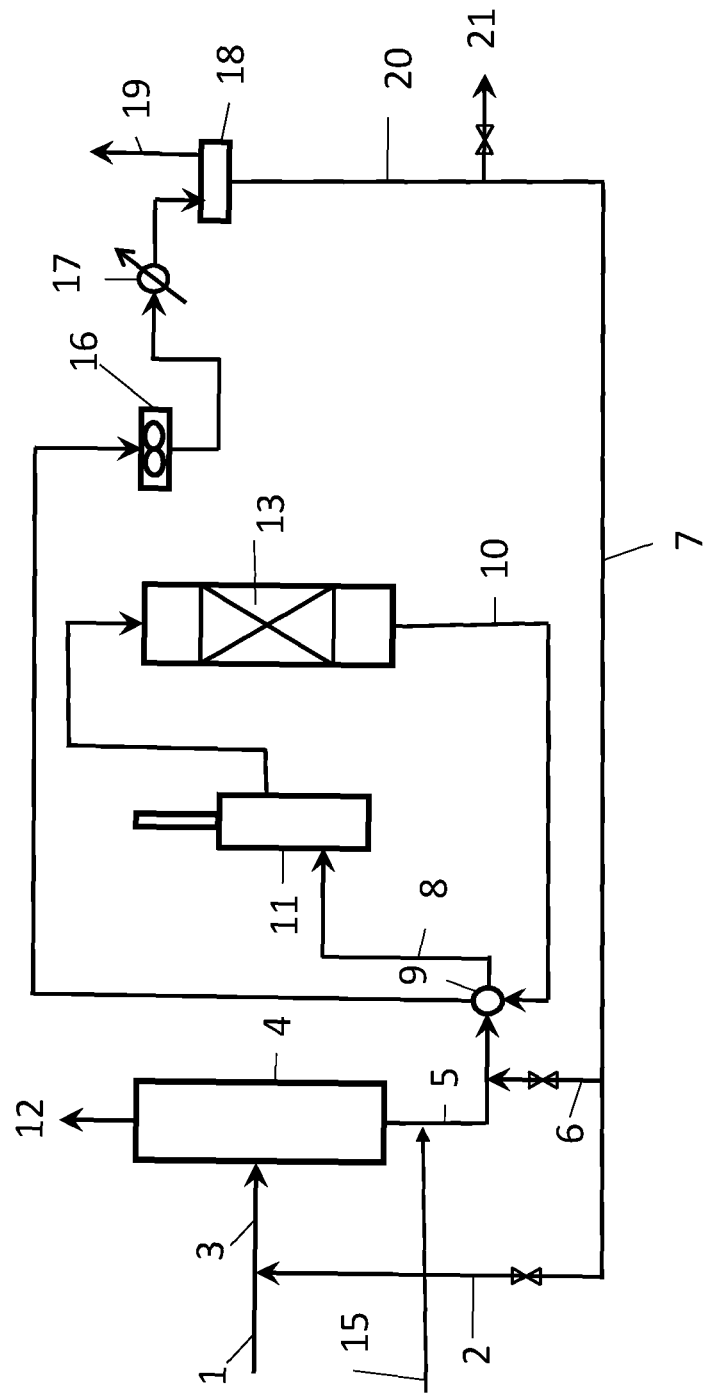

PROCESS TO PREPARE PROPYLENE

CROSS-REFERENCE TO RELATED APPLICATIONS

This application is a 35 U.S.C. § 371 National Phase Entry Application of International Application No. PCT/NL2017/050845 filed Dec. 19, 2017, which designates the U.S. and claims benefit under 35 U.S.C. § 119(a) of NL Provisional Application 2018256 filed Jan. 30, 2017 and under 35 U.S.C. § 119(e) of U.S. Provisional Application 62/437,242 filed Dec. 21, 2016, the contents of which are incorporated herein by reference in their entireties.

FIELD OF INVENTION

The invention is directed to a process to prepare propylene from a hydrocarbon feed comprising pentane.

BACKGROUND OF INVENTION

Such a process is described in US2009099398 titled "Pentane Cracking Process". The process is directed to prepare light olefins, such as propylene, from a paraffinic feed containing 4 to 6 carbons. The feed especially contains pentane and isopentane. These compounds are traditionally part of gasoline or motor fuel. Due to the low vapour pressure requirement for reformulated gasoline the presence of these pentane compounds has become undesirable. In the process of the prior art publication the paraffin feed comprising pentane is cracked to propylene in a series of packed bed reactors. The publication is silent regarding the type of cracking catalyst.

U.S. Pat. No. 5,171,921 describes a process wherein n-octane was cracked using a catalyst comprising of ZSM-5, a matrix and phosphorus. A high yield to propylene is disclosed and a low yield to C5 paraffins.

Applicants have tried to crack a hydrocarbon feed comprising pentane with a ZSM-5 based catalyst as in the prior art process and found that the conversion of the pentane compounds was low. The object of the present invention is to provide a process which can crack a hydrocarbon feed comprising pentane and wherein the conversion of pentane is increased.

SUMMARY OF THE INVENTION

The following process achieves this object. Process to prepare propylene from a hydrocarbon feed comprising pentane by contacting the hydrocarbon feed with a heterogeneous cracking catalyst as present in one or more fixed beds thereby obtaining a cracked effluent, wherein the heterogeneous catalyst comprises a matrix component and a molecular sieve comprising framework alumina, framework silica and a framework metal selected from the group of Zn, Fe, Ce, La, Y, Ga and/or Zr and wherein propylene is isolated from the cracked effluent.

Applicants found that with the process of the invention the conversion of normal pentane and iso-pentane can be significantly increased. Furthermore, the dry gas yield is lower and the selectivity of propylene relative to the total of C3-compounds is higher. This is especially advantageous in a recycle process wherein fraction of the cracked effluent boiling above the C3-compounds is recycled to the cracking process according to the invention.

SHORT DESCRIPTION OF THE FIGURE

FIG. 1 describes a process flow chart including a recycle

DETAILED DESCRIPTION OF THE INVENTION

The hydrocarbon feed may be any mixture of hydrocarbons comprising pentane. The pentane may be normal-pentane or iso-pentane or both. The content of the pentane may vary between 1 and 100 wt % and preferably between 20 and 80 wt %. The hydrocarbons are paraffins, aromatics naphthenic compounds and their mixtures. Preferably the content of olefins in the hydrocarbon feed is below 50 wt %, more preferably below 35 wt % The content of olefins having 4 or more carbon atoms in the hydrocarbon feed is suitably between 1 and 100 wt %, preferably between 1 and 70 wt % and even more preferably between 1 and 50 wt % and most preferred between 1 and 20 wt %. The content of aromatics is preferably below 5 wt %, more preferably below 2 wt % and most preferably below 0.5 wt %. An aromatics extraction step may be preferred if an intended feed contains more aromatic compounds. Such an aromatic extraction step will then be preferred to obtain a hydrocarbon feed having the preferred aromatic compounds. Suitably the hydrocarbon feed boils for more than 90 wt % between 35 and 250° C. The hydrocarbon feed will for its majority be comprised of hydrocarbons. Small amounts of for example water, sulphur compounds, nitrogen compounds may be present. The content of hydrocarbons in the feedstock will be above 95 wt %, suitably above 98 wt %. Examples of suitable hydrocarbon feeds will be described below. These feeds may be used as such or combined with the other illustrated feeds and/or combined with other hydrocarbon mixtures.

A preferred hydrocarbon feed is a mixture rich in iso-pentanes and/or normal-pentanes. Preferably such a mixtures comprises more than 50 wt % of iso-pentanes and/or normal-pentanes. The remaining compounds may be C4 and C6-hydrocarbons. Such mixtures may be obtained in a process to prepare motor gasoline having a low vapour pressure wherein the iso-pentanes and/or normal-pentanes are removed from the gasoline.

Another preferred hydrocarbon feed is a so-called light straight run (LSR) naphtha. This naphtha is obtained in a petroleum refinery as the overhead liquid distillate of the crude oil distillation unit which unit separates a crude petroleum feedstock. The straight run naphtha has not been subjected to any downstream processing such as hydrogenation, isomerisation, reforming, coking and (hydro)cracking. The LSR naphtha cannot be directly used as part of a gasoline product and typically requires severe processing in a Catalytic Reforming Unit which is not advantageous because this will limit the cycle length of said Catalytic Reformer. With the present process it is possible to convert this LSR naphtha directly into valuable products such as propylene.

Other preferred hydrocarbon feeds which are directly derived from a geological formation are natural gas liquids, shale oil derived hydrocarbon mixtures and tight oil derived hydrocarbon mixtures. By directly obtained is included any such geological derived mixtures which have been subjected to some sort of physical separation such as degassing, flashing or distillation.

Also hydrocarbon feeds boiling in the above referred to range are the fractions rich in hydrogen as isolated from the effluent of hydrotreating or hydrocracking processes may be used. Preferably hydrocarbon feeds isolated from the effluent of a refinery hydrogen depletion process, such as delayed cocker process and the fluid catalytic cracking process are used. More preferably hydrocarbon feeds as isolated from the effluent of a fluid catalytic cracking (FCC) process are used as the feedstock. Such a FCC unit is typically operated with propylene enhancing additional catalysts, like ZSM-5 comprising catalysts. The applicant has found that with the process of this invention a more efficient manner is obtained to prepare propylene. This allows to operate the FCC process itself without using the propylene enhancing additional catalysts and still prepare propylene in a high yield as calculated on fresh FCC feedstock. This is advantageous because less or no medium pore size zeolite is required to be supplied to the FCC process as replacement for degraded catalyst.

The heterogeneous catalyst comprises a matrix component and a molecular sieve comprising framework alumina, framework silica and a framework metal selected from the group of Zn, Fe, Ce, La, Y, Ga and/or Zr. Fe is preferred and combinations of Fe and Ga are preferably excluded. Suitable matrix materials are aluminum oxide, alumino silicate, silica, aluminium phosphate, silico aluminophosphate or a combination thereof. Silica and silica phosphate are preferred, silica most preferred. To the catalyst a clay can be added. The catalyst may comprise between 1 and 50 wt % of such a clay. Examples of suitable clays are montmorillonite, hectorite, beidellite, nontronite, saponite and laponite, a synthetic hectorite, or clays to improve physical properties, such as more elongated shaped clays.

Preferably the framework metal is selected from the group of Zn, Ga or Fe and more preferably Ga and/or Fe and most preferably Fe. The molecular sieve may further comprise extraframework iron compounds. In use the iron as initially present as part of the framework may extract from the framework and be comprised in the catalyst as extraframework iron compounds. The atomic ratio between framework Al and framework metal is preferably between 1:0.05 and 1:0.5. Preferably this ratio is below 0.4, more preferably below 0.2. Especially good results with respect to a low coke yield have been achieved at a ratio of between 0.05 and 0.1.

Applicants believe that by preparing the catalyst such that a metal as described above is present next to aluminium as part of the framework of the molecular sieve a pore structure is obtained which is beneficial for achieving a high yield in propylene and a good pentane conversion. As explained above part of the framework metal may extract from the framework. It is even believed that all of the metal may extract from the framework while the catalyst is still functioning as desired. For this reason the invention is also directed to a process to prepare propylene from a hydrocarbon feed comprising pentane by contacting the hydrocarbon feed with a heterogeneous cracking catalyst as present in one or more fixed beds thereby obtaining a cracked effluent wherein propylene is isolated from the cracked effluent. In this preferred process the heterogeneous catalyst comprises a matrix component and a modified molecular sieve comprising framework alumina and framework silica and wherein the catalyst is obtainable by (i) crystallization of a synthesis gel comprising $FeCl_3$ thereby obtaining a molecular sieve product comprising of framework Al, Si and Fe, (ii) calcining, (iii) mixing with the matrix and (iv) calcined until the molecular sieve had a framework Fe to framework Al molar ratio of less than 0.05.

The crystallization of a synthesis gel comprising $FeCl_3$ of step (i) may be performed as described by B. R. Wood et al./Journal of Catalysis 225 (2004) 300-306. The obtained crystals are calcined, after washing with a solution able to remove the Na from the zeolite, preferable an ammonium salt solution, preferably at a temperature of between 150 and 600° C., for at least 1 hours. In step (iii) the calcined crystals are mixed with a suitable matrix compound and the resulting sample is calcined in step (iv), preferably at a temperature between 350 and 700° C. for at least 0.5 hours such that the framework Fe to framework Al molar ratio is less than 0.05 and may even become zero. Such a catalyst may also be obtained by starting the cracking process using a catalyst having a framework Fe to framework Al molar ratio of more than 0.05. In the activation and regeneration cycles of the process it is found that Fe will leave the framework and a catalyst will be obtained having the desired framework Fe to framework Al molar ratio of less than 0.05.

Preferably the catalyst comprises phosphorus to improve its stability. Preferably phosphorus is introduced on the thus obtained catalyst to obtain a heterogeneous catalyst comprising between 0.5 and 10 wt % $P_2O_5$. Such impregnation can be performed prior to the mixing or shaping step (iii), during step (iii) or after performing step (iii). Optionally the impregnation step may be performed after calcination step (iv). If such phosphorus impregnation step is performed after step (iv) a final calcination after such impregnation is preferred. Preferably the heterogeneous catalyst comprises between 0.5 and 10 wt % $P_2O_5$. More preferred between 1 and 5 wt % $P_2O_5$.

The invention is also directed to a process to prepare propylene from a hydrocarbon feed comprising pentane by contacting the hydrocarbon feed with a heterogeneous cracking catalyst as present in one or more fixed beds thereby obtaining a cracked effluent wherein propylene is isolated from the cracked effluent.

The content of the modified molecular sieve in the heterogeneous catalyst is preferably between 10 and 75 wt %. Though applications can be envisioned where the catalyst solely consists of zeolite, such as a membrane grown out of zeolites.

The molecular sieve may be a modified MFI, FER or MOR type or combinations thereof. The modification is that part of the framework alumina of the MFI, FER or MOR type molecular sieve is substituted by the framework metal. Preferably the molecular sieve is of the MFI type. A well-known example of a MFI type molecular sieve is ZSM-5.

The silica to alumina atomic ratio (SAR) of the molecular sieve is suitably between 20 and 300. If the SAR of the molecular sieve is too low well known dealumination steps may be performed to dealuminate the molecular sieve. Examples of dealumination steps are steaming and leaching.

The molecular sieve is present in the heterogeneous catalyst as crystals having a size smaller than 100 nm, more preferentially smaller than 70 nm and most preferred smaller than 50 nm as measured by XRD.

The heterogeneous catalyst may be prepared by the process described above or by any other process. For example when another metal than Fe is used comparable catalyst preparation methods may be used known to the skilled person.

The process is performed by contacting a hydrocarbon feed comprising pentane with a heterogeneous cracking catalyst as present in one or more fixed beds. The temperature in the one or more fixed beds is suitably between 300 and 750° C., more preferred between 300 and 700° C. and most preferred between 450 and 600° C. The absolute pressure is suitably between 0.05 and 10 MPa and preferably between 0.1 and 0.5 MPa. It is preferred to reduce residence time, suppress coke make and reduce hydrocarbon partial pressure via dilution of steam. The reduction in hydrocarbon partial pressure boosts the dehydrogenation reaction, suppresses the reverse reaction, and suppresses the recombination of light olefins.

The weight hourly space velocity, WHSV, as expressed in mass flow (per hour) divided by the mass of the catalyst is preferably higher than 20/hour and more preferably higher than and including 50/hour. Applicants found that by increasing the WHSV even more the olefin yield remains high while allowing the use of smaller reactor vessels. Therefore, a WHSV of above 100/hour is most preferred. This allows in use a lower feed rate than the design feed rate and still maintaining a high olefin yield. The feed is the hydrocarbon feed and any optional diluents, eg inert diluents. For example, a 30% dilution with nitrogen results in an increase of 30% in WHSV.

The process is carried out in one or more packed beds. By more than one bed is here meant any packed beds which are arranged in series with respect to each other. A similar second or even a third set of packed bed or beds may be arranged parallel to said first bed or beds. These second or third bed or beds may be used for performing the process according to the invention when the first bed or beds are regenerated to remove coke and optionally other contaminants. An example of such a regeneration process is when the reactors are operated as a simulated moving bed. It is also conceivable that not all packed beds in one set of beds in series are regenerated at a time. Instead a packed bed in a set of packed beds may have a longer run time as a result of the different catalyst composition with the packed bed and thus require less frequent regeneration than the remaining beds in the same in-series configuration.

If more than one packed bed in series is used to perform the process it may be advantageous to remove some of the low boiling reaction products including propylene from the reaction mixture in between the packed beds. This may be performed by means of a flash separation. The low boiling gasses thus obtained may be provided to a separation unit in which propylene is isolated from the reaction products of the most down-stream packed bed as will be described in more detail below. The higher boiling fraction as obtained in such a separation may be provided to the next bed or even internally recirculated to one or more of the up-stream beds, optionally after reheating this fraction. The chosen recycle will depend on the olefin content in such a higher boiling fraction and the catalyst gradient in the packed beds. Such a direct recycle may also be performed with the higher boiling fraction as obtained when low boiling gasses are separated from the final effluent of the one or more packed beds.

The propylene is isolated from the cracked effluent. Other compounds will suitably also be isolated from the cracked effluent. Such compounds are for example ethane, ethylene, hydrogen and any water, propane and butylenes. Such a separation may include distillation and/or flash separation. Because the selectivity of propylene on the total of propylene and propane is improved less propane is formed. This is advantageous because a less difficult propylene and propane separation will be required to obtain for example a polymer grade propylene. In this separation ethylene may be isolated from the low boiling compounds. The C4 fraction including butane and butylene may be recovered as such or be recycled together with the higher boiling compounds to the packed bed or beds as described below. Suitably a higher boiling fraction will be obtained after the above described isolation step and will comprise for more than 90 wt % of hydrocarbons boiling above 75° C.

Any low boiling fractions separated from intermediate streams between the packed beds as described above may be fed to the above described isolation step. Such a fraction may contain some high boiling compounds because of the coarse separation between said beds. By feeding this fraction to this isolation step these high boiling compounds are recovered to be combined with the higher boiling fraction.

The higher boiling fraction as obtained after isolation of propylene and possible other low boiling compounds from the cracked effluent is preferably recycled to the one or more fixed beds. In this manner the high boiling fraction is contacted in admixture with the hydrocarbon feed with the heterogeneous cracking catalyst. Preferably the higher boiling fraction is first subjected to an isomerization step before being recycled to the one or more fixed beds. It has been found that the propylene yield may increase when such an isomerisation step is performed. Isomerisation of especially the normal pentanes and normal hexanes to their branched isomers has been found to increase the propylene yield.

The isomerization step may be performed by known isomerization processes which are preferably performed in the presence of hydrogen and a chlorided platinum alumina catalyst or a platinum-zeolitic catalyst as described below. The hydrogen and high boiling fraction is contacted in a reaction zone with the isomerization catalyst. The catalyst composites that can be used in the isomerization zone include traditional isomerization catalysts. A preferred isomerization catalyst is a chlorided platinum alumina catalyst as for example described in U.S. Pat. No. 5,245,102 as also incorporated herein by reference. The aluminum is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 weight percent of the platinum. Other platinum group metals may be present in a concentration of from 0.1 to 0.25 weight percent. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 10 weight percent based upon the dry support material. The use of chloride in amounts greater than 5 weight percent have been found to be the most beneficial for this process. The inorganic oxide preferably comprises alumina and more preferably gamma-alumina, eta-alumina, and mixtures thereof.

Another preferred isomerization catalyst composition comprises a Group VIII noble metal, a hydrogen form crystalline aluminosilicate and a refractory inorganic oxide as for example described in U.S. Pat. No. 5,245,102 as also incorporated herein by reference. The catalyst composition suitably has a surface area of at least 580 $m^2/g$ and preferably above 580 $m^2/g$. A preferred Group VIII noble metal is platinum. The Group VIII noble metal is present in an amount from about 0.01 to 5 percent by weight of the composite and preferably in an amount of at least 0.15 percent by weight but not over 0.35 percent by weight. The zeolitic catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form and MFI-type zeolites, like ZSM-5, are preferred.

The above isomerization catalysts may be sensitive to sulfur and oxygen-containing compounds. Therefore, the use of such catalysts requires that the high boiling fraction be relatively free of such compounds. A sulfur concentration no greater than 0.5 ppm is generally required. The presence of sulfur in the high boiling compounds serves to temporarily deactivate the catalyst by platinum poisoning. Water can act to permanently deactivate the chlorided platinum alumina catalyst by removing high activity chloride from the catalyst and replacing it with inactive aluminum hydroxide. Therefore, water, as well as oxygenates, in particular C1-05 oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the high boiling fraction by hydrotreating. A variety of commercial dryers are available to remove water from the feed components. Adsorption processes for the removal of sulfur and water from hydrocarbon streams are also well known to those skilled in the art.

Hydrogen is admixed with the high boiling compounds in an amount that will provide a hydrogen to hydrocarbon molar ratio of from 0.01 to 10 in the effluent from the isomerization zone. Preferably, the hydrogen to hydrocarbon ratio is in the range of 0.05 to 5. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics, cracking and disproportionation. For high boiling compound mixtures having a high level of unsaturates, satisfying the stoichiometric hydrogen will require a higher hydrogen to hydrocarbon ratio for the feed at the inlet of the isomerization zone. Optionally a hydrogenation step upstream the isomerization step may be performed to saturate these unsaturated compounds. Hydrogen in excess of the stoichiometric amounts for the side reactions is often maintained in the reaction zone to provide stability and conversion by compensating for variation in feedstream compositions that alter the stoichiometric hydrogen requirements.

Operating conditions within the isomerization zone are selected to maximize the production of isoalkane product from the feed components. Temperatures within the reaction zone will usually range from 40 to 320° C. and preferably 60 to 160° C. Pressure conditions in the isomerization of C4-C6 paraffins range from 0.7-7 MPa and preferably 2-3 MPa. The feed rate to the reaction zone can also vary over a wide range. These conditions include liquid hourly space velocities ranging from 0.5 to 12 $hr^{-1}$, however, space velocities between 1 and 6 $hr^{-1}$ are preferred. The isomerization zone will usually operate at a LHSV of about 1.5.

From the effluent of the isomerization step hydrogen, butane and lighter gaseous compounds may be separated in one or more steps before recycling this effluent to the cracking reactor.

The higher boiling fraction or part of it may also be used as part of a gasoline motor fuel or as feedstock for a refinery treating process such as isomerization, catalytic cracking and/or reforming. Preferably at least a small part of the higher boiling fraction is not recycled. Such a purge can avoid the build-up of compounds which are difficult to convert in the cracking process. The minimal amount of such a purge stream will depend on the hydrocarbon feed and process conditions and can be easily determined by a skilled person.

The hydrocarbon feed preferably has an aromatics content, i.e. a benzene, toluene and xylene content, of below 20 wt % and even more preferably below 10 wt % as being fed to the packed bed or beds. Thus preferably the hydrocarbon feed is obtained as the aromatic poor effluent of an aromatics extraction step of an aromatic rich feedstock.

When the process involves the here described recycle of higher boiling compounds it is preferred that the hydrocarbon feed in admixture with the above described recycle stream of high boiling compounds has an aromatics content, i.e. a benzene, toluene and xylene content, of below 20 wt % and even more preferably below 10 wt % as being fed to the packed bed or beds. If the intended feed of the process contains a high amount of aromatics it is preferred to separate these compounds prior to the cracking step. In this situation it is preferred to obtain the hydrocarbon feed as the aromatic poor effluent of an aromatics extraction step of an aromatic rich feedstock. But even if the hydrocarbon feed itself does not contain high amounts of aromatics these compounds may still be formed in the cracking process according to the invention.

The high boiling fraction which is recycled to the one or more fixed beds of the cracking step may be partly or in whole be subjected to an aromatics extraction step if the content of aromatics in the high boiling fraction is high. Applicants found that aromatics are formed in the cracking process according the invention for certain feeds while considerably less aromatics is formed for other feeds. It will be straightforward for the skilled person to find the optimal recycle process configuration for a given feed such that the content of aromatics in the feed to the fixed beds is within the preferred low ranges while trying to minimise the part of the higher boiling fraction which requires an aromatics extraction. Therefore between 0 and 100 wt % of the, optionally isomerized, higher boiling fraction as isolated from the cracked effluent may be subjected to an aromatics extraction step. All or part of the optionally remaining higher boiling fraction is directly is recycled to the one or more fixed beds. Preferably the aromatic extraction step for this recycle stream is the same aromatics extraction step which treats the earlier referred to aromatic rich feedstock.

A suitable aromatics extraction step separates more than 90 wt % of the combined benzene, toluene and xylene from its feed. Such an aromatics extraction step is well known and examples of suitable extraction solvents are diethylene glycol, tetraethylene glycol, diethylene glycol, dimethyl sulfoxide, sulfolane, N-formyl morpholine, N-methyl pyrrolidone, a glycol-glycol ether mixture and tertrahydrothiophene 1-1 dioxide. Because olefins may be present in the feed to the extraction step an aromatic extraction process is preferred which is selective for aromatics in the presence of olefins. A suitable extraction process is an extractive distillation using one of the above described solvents and suitably sulfolane, N-formyl morpholine or N-methyl pyrrolidone, optionally in combination with a suitable co-solvent. A suitable commercially available process is the so-called GT-BTX PluS type as developed and offered by GTC Technology, Houston Tex.

The invention is also directed to a process to prepare propylene from a hydrocarbon feed comprising pentane by contacting the hydrocarbon feed with a heterogeneous cracking catalyst as present in one or more fixed beds thereby obtaining a cracked effluent, wherein propylene is isolated from the cracked effluent to obtain a higher boiling fraction and wherein part or all of this higher boiling fraction is subjected to an isomerization step to obtain an isomerised higher boiling fraction which isomerised higher boiling fraction is recycled to the one or more fixed beds to be contacted in admixture with the hydrocarbon feed with the heterogeneous cracking catalyst. Applicant has found that when an isomerisation is part of such a process the yield to propylene can be improved.

The heterogeneous cracking catalyst may be the catalyst as described, ie the innovative catalyst, or as described below. The heterogeneous cracking catalyst may suitably comprise an acidic material. Suitable acidic materials are those which can crack the gasoline range olefins to propylene. Such an acidic material may be a molecular sieve or a material having strong acid sites. A first type of heterogeneous cracking catalyst does not comprise a molecular sieve and does comprise a material having strong acid sites as the acidic material. A suitable acidic material is an amorphous or semi-crystalline material chosen from the group of heteropoly acids, alumina, boehmite alumina, gamma alumina, theta alumina, silica alumina, silica-titania, silica-tungsten, silica phosphorous, silica-alumina-phosphorous. The acidic material may also be a molecular sieve. An advantage of a molecular sieve is the high acid site density per reactor volume.

If a molecular sieve is used it is preferred that an optional carrier as part of the catalyst particles may have no strong acid sites, some strong acid sites or only strong acids sites. The choice of suitable optional carrier will depend on the composition of the feedstock. Preferably the carrier does not have strong acid sites. The molecular sieve may have 8-membered oxygen ring channels such as Chabazite, also referred to as CHA structure type according to the Atlas of zeolite structure types, $4^{th}$ rev. ed/W. M. Meier, D. H. Olson and Ch. Baerlocher. A typical example of such a molecular sieve is SAPO-34. The molecular sieve is suitably an intermediate pore-size zeolite. The term "intermediate pore-size zeolite" is meant to indicate any zeolite of which the pore size is intermediate between the pore size of a small pore-size zeolite such as typically A-type zeolite, and the pore size of a large pore-size zeolite such as typically mordenite, or X-type or Y-type zeolite". The intermediate pore size zeolite has a 10 or 12-membered oxygen ring in the crystal structure thereof. The zeolite suitably has a silica to alumina ratio between 10-300 and more preferred between 10-50. Examples of the intermediate pore-size zeolite are ZSM-5, ZSM-8, ZSM-11, ZSM-12, ZSM-21, ZSM-23, ZSM-35, ZSM-38. Preferably the molecular sieve is chosen from the structure types having a 10-ring channels according to structure types MFI, MEL, IMF, TUN and EUO. MFI is also known as ZSM-5, MEL is known as ZSM-11, IMF is known as IM-5 and TUN is known as TNU-9. Of this list MFI is most preferred in view of its availability combined with its performance.

The above molecular sieves may be present as such to provide the cracking catalyst. Suitably the molecular sieve is comprised in a carrier, wherein the weight content of the molecular sieve in the heterogeneous catalyst is between 5 and 70 wt %. The carrier may be silica, silica-alumina or alumina and may be suitably treated with phosphorous as described for the innovative catalyst.

The process is performed by contacting a hydrocarbon feed comprising pentane with the heterogeneous cracking catalyst as present in one or more fixed beds. The temperature in the one or more fixed beds is suitably between 300 and 750° C., more preferred between 300 and 700° C. and most preferred between 450 and 600° C. The absolute pressure is suitably between 0.05 and 10 MPa and preferably between 0.1 and 0.5 MPa. It is preferred to reduce residence time, suppress coke make and reduce hydrocarbon partial pressure via dilution of steam. The reduction in hydrocarbon partial pressure boosts the dehydrogenation reaction, suppresses the reverse reaction, and suppresses the recombination of light olefins.

The weight hourly space velocity, WHSV, as expressed in mass flow (per hour) divided by the mass of the catalyst is preferably higher than 20/hour and more preferably higher than and including 50/hour. Applicants found that by increasing the WHSV even more the olefin yield remains high while allowing the use of smaller reactor vessels. Therefore, a WHSV of above 100/hour is most preferred. This allows in use a lower feed rate than the design feed rate and still maintaining a high olefin yield. The feed is the hydrocarbon feed and any optional diluents, eg inert diluents. For example, a 30% dilution with nitrogen results in an increase of 30% in WHSV.

As in the earlier described process it is also preferred to use a hydrocarbon feed as obtained as the aromatic poor effluent of an aromatics extraction step of an aromatic rich feedstock. The preferred composition of the earlier feed also applies for this process. Further it is preferred that between 50 and 100 wt % of the isomerised higher boiling fraction as isolated from the cracked effluent is subjected to the aromatics extraction step and all or part of the remaining isomerised higher boiling fraction is directly recycled to the one or more fixed beds to be contacted in admixture with the hydrocarbon feed with the heterogeneous cracking catalyst. Further the isomerisation may be performed as described above.

Figures

FIG. 1 shows a process scheme for a process to prepare propylene according to one embodiment of the present invention. Via stream 1 a fresh hydrocarbon feed boiling between 35 and 250° C. is mixed with a recycle stream 2 to obtain a combined stream 3. Combined stream 3 is fed to an aromatics extraction unit 4 in which benzene, toluene and xylene are extracted from the mixture of hydrocarbons thereby obtaining a mixture of hydrocarbons poor in aromatics in stream 5 and a stream 12 comprising these aromatic compounds. The mixture of hydrocarbons poor in aromatics in stream 5 is mixed with a second recycle stream 6 to obtain a hydrocarbon feed stream 8. The composition of recycle stream 2 and recycle stream 6 are the same in the process of this FIGURE. The mass flow of stream 2 and 6 may be different such that stream 2 is at least 5 wt % of the combined streams 2 and 6 (stream 7) and preferably between 10 and 30 wt % of the combined streams 2 and 6 (stream 7).

When a fresh hydrocarbon feed contains no or very little aromatic compounds, like for example a feed rich in pentanes, the fresh feed may be directly fed to packed bed reactor 13 via stream 15.

Feedstock stream 8 is raised in temperature in an indirect heat exchanger 9 against hot reactor effluent stream 10. The partly heated feedstock stream 8 is further increased in temperature in furnace 11 before being fed to the packed bed reactor 13 comprising the heterogeneous cracking catalyst. The furnace 11 may use for example fuel gas or fuel oil as fuel.

The cracked effluent as being discharged from packed bed reactor 13 in stream 10 will comprise the desired propylene and ethylene, butylene and a higher boiling fraction comprising non-reacted feed stock and small amounts of aromatic by-products. The cracked effluent in stream 10 is reduced in temperature in indirect heat exchanger 9, air coolers 16 and chilled water trim coolers 17. Other methods of cooling are also possible. Propylene in stream 19 and optionally other valuable lower olefins may be separated from the cracked effluent in a single stage flash separation 18. Alternatively, propylene and other olefins may be separated from the cracked effluent by means of one or more distillation columns or any other process sufficient to separate the light olefin product from the cracked effluent. From the remaining higher boiling fraction in stream 20 a part may be discharged as a purge via stream 21 to avoid a build-up of inert materials in the recycle stream. The remaining higher boiling fraction in stream 7 may be recycled to the aromatics extraction unit 3 and directly to the packed bed reactor 13 as described above.

A by-product of the cracking reaction is coke as deposited on the heterogeneous cracking catalyst. The packed beds of catalysts may therefore require some sort of regeneration to burn the coke in the presence of oxygen into $CO_2$. A second reactor will be on stand-by for operation when the first reactor requires regeneration. The reactor just taken out of service will then be regenerated in preparation for its next cycle when the present reactor requires regeneration. This process will thereby continue without interruption.

The invention shall be illustrated by the following non-limiting examples.

Example 1

Two MFI molecular sieves were prepared, namely a MFI-molecular sieve and a Fe-MFI-molecular sieve which comprises framework iron (Fe). The sieves were prepared in the following manner. Ammonium fluoride, tetrapropalammonium bromide, aluminum nitrate, and water were placed in Teflon-lined bomb reactors. For Fe-MFI and Fe/Al-MFI, FeCl3 was also added. The mixtures were then stirred until all solids dissolved. Ludox LS-30 was then added to each mixture and the reactors were placed in an oven at 433° K for 7 days. The resulting materials were calcined in air at 773° K for 3 h after an 2-h ramp, also in air. The MFI products were then ion-exchanged with 1 M ammonium nitrate, washed with deionized water, and dried overnight at 393° K. The crystal samples were activated by calcining in air at 873° K for 2 h after an 2-h ramp.

Catalysts were prepared by mixing 70 parts dry base of the obtained crystal samples with 30 parts dry base Catapal alumina, water and nitric acid (70% strength) was used as peptizing agent. The paste was spread on a plate and dried in air overnight at 393° K. The samples were calcined in air at 873° K for 2 h after an 2-h ramp. The samples were crushed to millimetre sized shapes and impregnated with ammonium phosphate solution (2.5 wt % P2O5 on catalyst) and dried overnight at 393° K. The samples were activated by calcining in air at 873° K for 2 h after an 2-h ramp.

Example 2

A packed bed reactor was provided consisting of the MFI catalyst obtained in Example 1. A naphtha having a GC RON of 91.2 with 90% boiling point at 182° C. consisting of 35 wt % paraffins, 12 wt % naphthenes, 31 wt % olefins and 22 wt % aromatics and 1.4 wt % normal pentane and 10.1 wt % iso-pentane was fed to the reactor at 1.4 g/min in 50 ml/min nitrogen at 500° C. The WHSV was 57 h-1. The pressure at the reactor effluent was atmospheric. The cracked effluent was analysed and the results presented as (in weight percentages) are provided in Table 1.

Example 3

Example 2 was repeated except that the catalyst was the Fe-MFI catalyst obtained in Example 1. The cracked effluent was analysed and the results presented as (in weight percentages) are provided in Table 1.

TABLE 1

| | Example 2 | Example 3 |
|---|---|---|
| H2, methane, and C2-hydrocarbons (dry gas) (wt % on feed) | 1.8 | 1.3 |
| Propylene/(total of C3 hydrocarbons) (wt/wt) | 0.91 | 0.95 |
| Butylene/(total of C4 hydrocarbons) (wt/wt) | 0.89 | 0.94 |
| GC RON of C5-216° C. | 91.2 | 91.5 |
| Normal pentane (wt % on feed) | 0.8 | 0.5 |
| Iso-pentane (wt % on feed) | 5.2 | 2.4 |
| benzene (wt % on feed) | 0.12 | 0.05 |

The invention claimed is:

1. A process to prepare propylene from a hydrocarbon feed comprising pentane by contacting the hydrocarbon feed with a heterogeneous cracking catalyst as present in one or more fixed beds thereby obtaining a cracked effluent,
    wherein the heterogeneous catalyst comprises a matrix component and a molecular sieve of the MFI type comprising framework alumina, framework silica and framework Fe
    wherein the atomic ratio between the framework alumina and the framework Fe is between 1:0.05 and 1:0.5;
    wherein the heterogeneous catalyst comprises between 0.5 and 10 wt % $P_2O_5$;
    wherein propylene is isolated from the cracked effluent; and
    wherein the temperature in the one or more fixed beds is between 300 and 750° C. and the absolute pressure is between 0.1 and 10 MPa, and wherein the Weight Hourly Space Velocity (WHSV) is higher than and including 50/hour.

2. The process according to claim 1, wherein the content of the modified molecular sieve in the heterogeneous catalyst is between 10 and 75 wt %.

3. The process according to claim 1, wherein the matrix is aluminum oxide, alumino silicate, silica, aluminium phosphate, silico aluminophosphate or a combination thereof.

4. The process according to claim 1, wherein the SAR of the molecular sieve is between 20 and 300.

5. The process according to claim 1, wherein the heterogeneous catalyst comprises between 1 and 5 wt % $P_2O_5$.

6. The process according to claim 1, wherein the molecular sieve is present in the heterogeneous catalyst as crystals having a size smaller than 100 nm as measured by XRD.

7. The process according to claim 6, wherein the molecular sieve is present in the heterogeneous catalyst as crystals having a size smaller than 70 nm as measured by XRD.

8. The process according to claim 7, wherein the molecular sieve is present in the heterogeneous catalyst as crystals having a size smaller than 50 inn as measured by XRD.

9. The process according to claim 1, wherein the temperature in the one or more fixed beds is between 450 and 600° C. and the absolute pressure is between 0.1 and 0.5 MPa.

10. The process according to claim 1, wherein a higher boiling fraction is obtained when propylene is isolated from the cracked effluent and wherein part or all of this higher boiling fraction is recycled to the one or more fixed beds to be contacted in admixture with the hydrocarbon feed with the heterogeneous cracking catalyst.

11. The process according to claim 10, wherein the higher boiling fraction is first subjected to an isomerization step before being recycled to the one or more fixed beds.

12. The process according to claim 1, wherein the hydrocarbon feed is obtained as the aromatic poor effluent of an aromatics extraction step of an aromatic rich feedstock.

13. The process according to claim 1, wherein the hydrocarbon feed comprises between 1 and 20 wt % olefins having 4 or more carbon atoms.

14. The process according to claim 13, wherein the hydrocarbon feed is a mixture of paraffins, olefins, naphthenic and aromatic compounds boiling for more than 90 wt % between 35 and 250° C.

15. The process according to claim 14, wherein the hydrocarbon feed comprises a light straight run naphtha and/or a fraction as isolated from the effluent of any one of the following processes and optionally subjected to an aromatics extraction wherein the processes include Fluid Catalytic Cracking, Catalytic Polymerization, Hydrotreating, Hydrocracking and/or Delayed Coking.

16. The process according to claim 15, wherein the hydrocarbon feed comprises a light straight run naphtha.

17. The process according to claim 15, wherein the hydrocarbon feed comprises a fraction as isolated from the effluent of a Fluid Catalytic Cracking process.

18. The process according to claim 1, wherein the mixture of hydrocarbons comprises more than 5 wt % paraffins having 5 carbon atoms.

19. The process according to claim 18, wherein the mixture of hydrocarbons comprises more than 50 wt % paraffins having 5 carbon atoms.

20. The process according to claim 1, wherein the hydrocarbon feed is obtained as the aromatic poor effluent of an aromatics extraction step of an aromatic rich feedstock.

* * * * *